United States Patent [19]

Eitan et al.

[11] Patent Number: 5,565,462
[45] Date of Patent: Oct. 15, 1996

[54] COMPOSITION FOR TOPICAL TREATMENT OF PSORIASIS AND ATOPIC DERMATITIS COMPRISING A XANTHINE DERIVATIVE

[75] Inventors: Anat Eitan, Even Yehuah; Rachel Nachman; Sasson Cohen, both of Tel-Aviv, all of Israel

[73] Assignees: Teva Pharmaceutical Industries, Ltd., Jerusalem; Ramot University for Applied Research and Industrial Development, Ltd., Tel-Aviv, both of Israel

[21] Appl. No.: 263,399

[22] Filed: Jun. 21, 1994

Related U.S. Application Data

[63] Continuation of Ser. No. 934,268, Aug. 25, 1992, abandoned.

[30] Foreign Application Priority Data

Sep. 2, 1991 [IL] Israel .......................... 99368

[51] Int. Cl.$^6$ .................................................. A61K 31/52
[52] U.S. Cl. .................................. 514/262; 514/263
[58] Field of Search ................................... 514/262, 263

[56] References Cited

U.S. PATENT DOCUMENTS

| Re. 33,107 | 11/1989 | Dikstein et al. ........................ 514/46 |
| 4,141,976 | 2/1979 | Voorhees ................................ 424/240 |
| 4,341,783 | 7/1982 | Scheindlin ............................. 424/253 |
| 4,369,181 | 1/1983 | Miller et al. .......................... 514/167 |
| 4,594,432 | 6/1986 | Baggiolini et al. .................... 459/214 |
| 4,612,308 | 9/1986 | Baggiolini et al. .................... 514/167 |
| 4,617,279 | 10/1986 | Manabe et al. ........................ 501/10 |
| 4,711,881 | 12/1987 | Ikekawa .................................. 514/167 |
| 4,716,165 | 12/1987 | Abov-Gharbia et al. . |
| 4,719,205 | 1/1988 | DeLuca et al. ......................... 514/167 |
| 4,804,502 | 2/1989 | Baggiolini et al. .................. 260/397.2 |
| 4,832,875 | 5/1989 | Ikekawa .................................. 514/167 |
| 4,851,401 | 7/1989 | DeLuca et al. ......................... 514/167 |
| 4,868,165 | 9/1989 | Ikekawa .................................. 514/167 |
| 4,938,960 | 7/1990 | Ismail . |
| 5,096,906 | 3/1992 | Mandell et al. ....................... 514/263 |
| 5,190,935 | 3/1993 | Binderup et al. . |
| 5,194,431 | 1/1983 | DeLuca et al. ......................... 514/167 |
| 5,196,429 | 3/1993 | Mandell et al. ....................... 514/263 |
| 5,200,536 | 4/1993 | Ikekawa et al. ........................ 552/653 |
| 5,260,290 | 11/1993 | DeLuca et al. ......................... 514/167 |
| 5,292,728 | 3/1994 | Neef et al. ............................. 514/167 |

FOREIGN PATENT DOCUMENTS

| 0158090 | 2/1985 | European Pat. Off. . |
| 0195496 | 9/1986 | European Pat. Off. . |
| 0260127 | 3/1988 | European Pat. Off. . |
| WO89/05145 | 6/1989 | WIPO . |
| WO91/01730 | 2/1991 | WIPO . |

OTHER PUBLICATIONS

Chemical Abstracts 107:223073e (1987).
Journal of Clinical Endocrinology and Metabolism, vol. 70, No. 6, pp. 1687–1692, 1990.
J. Allergy Clin. Immunol, Dec. 1990, vol. 86, No. 6, Part 1, pp. 881–885.
Dermatologic Clinics–vol. 6, No. 4, Oct. 1988, pp. 585–608, Haines Ely, M.D. Pentoxifylline Therapy in Dermatology.
Drug Therapy, Apr. 1987, pp. 29–38, Jeffrey P. Callon, M.D. Papulosquamous Lesions.
J. Allergy Clin. Immunol, Mar. 1973, vol. 51, No. 33, pp. 139–151, Halpern et al Development of childhood allergy in infants fed breast, soy, or cow milk.

*Primary Examiner*—Kimberly J. Prior
*Attorney, Agent, or Firm*—Oliff & Berridge

[57] ABSTRACT

Use of a compound selected from the group consisting of pentoxifylline, propentofylline and torbafylline for topical treatment of psoriasis or atopic dermatitis and pharmaceutical compositions comprising them.

4 Claims, 2 Drawing Sheets

COMPOSITION FOR TOPICAL TREATMENT OF PSORIASIS AND ATOPIC DERMATITIS COMPRISING A XANTHINE DERIVATIVE

This is a Continuation of application Ser. No. 07/934,268 filed Aug. 25, 1992, now abandoned.

FIELD OF THE INVENTION

This invention relates to topical pharmaceutical compositions for and a method of treating inflammatory and proliferative skin diseases such as psoriasis and atopic dermatitis.

BACKGROUND OF THE INVENTION

Psoriasis is a common chronic relapsing inflammatory skin disease which affects 1–3% of the population. It is characterised by the circumscribed scaling erythematous plaques of various sizes and forms which in some cases may extend to more than 50% of the skin area. The psoriatic condition is composed of two main processes: cellular hyperproliferation and inflammation. Despite extensive research the etiology of the disease is still unknown.

Psoriasis is currently treated by a number of methods which include topical applications consisting of tar derivatives, steroids, vitamin D and its derivatives or vitamin A and its derivatives (J. P. Callen, Drug Therapy, April 1987, pp. 29–35). These therapies are only partially successful and may be accompanied by undesired side affects. Thus although steroids can be very effective, they are also frequently associated with side effects. Other therapies include phototherapy with or without concomitant systemic administration of psoralen derivatives. Additionally, systemic administration of steroids, methotrexate and cyclosporine have been used for treatment of severe cases of psoriasis. All of these therapies are associated with side effects. There is thus an urgent need for new effective, non-toxic therapeutics for psoriasis.

Atopic dermatitis is a chronic skin condition of unknown etiology, and which may be continuous from infancy to adulthood. There is about 4% incidence of atopic dermatitis from birth to 7 years (Halpern et al., J. Allergy Clin. Immunol. 51:139–151 (1973). In childhood, it is characterized by papules, erythema, thickening and lichenification. In the adolescent, the main symptoms are thickening and lichenification with erythema and scaling. Pruritus is a general feature of the disease. Systemic therapy includes antihistamine drugs and steroids, but the latter are reserved for unmanageable cases and used for the shortest period possible. Topical therapy includes fluorinated and fluorochlorinated corticosteroid preparations, but striae and cataracts are likely complications. Clearly there is as yet no satisfactory and safe drug treatment for atopic dermatitis.

Xanthine derivatives have been proposed for the treatment of psoriasis and atopic dermatitis. U.S. Pat. No. 4,141,976 proposes certain pharmaceutical preparations for the topical treatment of psoriasis. Among the compounds described are certain substituted alkylxanthine derivatives and substituted thioxanthines. However data demonstrating effectiveness is shown only for RO 20-1724 (d,1-4-(3-butoxy-4-methoxybenzyl)- 2-imidazolidinone, which is not a xanthine derivative. There is no data showing that the xanthine derivatives are effective therapeutics when topically administered to patients suffering from proliferative skin disease.

WO 9101730 describes the use of certain xanthine derivatives for the treatment of asthma, urticaria, eczema and rhinitis. Suggested modes of administration are listed as oral, rectal, topical, parenteral, intravenous, or intramuscular or through the respiratory tract. EP 195,496 describes the use of certain xanthine derivatives for treating proliferative skin disease such as psoriasis. The xanthine derivatives are administered orally. U.S. Pat. No. 4,716,165 describes the use of certain theobromine derivatives for treating asthma, allergic rhinitis, atopic dermatitis or eczema. WO 8905145 describes the use of certain xanthine derivatives for the treatment of a wide variety of disease states including psoriasis. EP 260,127 describes the oral administration of certain xanthine derivatives for the treatment of proliferative skin disease. U.S. 4,341,783 describes the use of topical dyphylline for the treatment of psoriasis. There is no teaching or suggestion in any of the above-listed patents and patent applications that the topical administration of the compounds of the instant invention would be more effective in the treatment of psoriasis or atopic dermatitis than the topical application of other xanthine derivatives described in the above-cited patents and patent applications.

Ravid et al. (Ravid et al., J. Allergy Clin. Immunol. 86:881–885 (1990) and J. Clin. Endocrinol. Metab. 70:1687–1692 (1990)) have shown that certain compounds which increase the levels of cyclic adenosine monophosphate (cAMP) are capable of inhibiting the mitogenic induced proliferation of peripheral blood mononuclear cells (PBMC) from both healthy and atopic patients. The only xanthine derivative tested in these articles was isobutylmethylxanthine (IBMX). However, there is no teaching or suggestion in these publications that other xanthine derivatives may have different or superior properties to IBMX. There is certainly no mention of pentoxifylline (PTX), propentofylline (PPF) or torbafylline (TBF).

Pentoxifylline (PTX) (3,7-dimethyl-1-(5-oxohexyl)-xanthine), propentofylline (PPF) (3-methyl-7-propyl-1-(5-oxohexyl)-xanthine) and torbafylline (TBF) (3-methyl-7-ethoxymethyl-1-( 5-hydroxy-5-methylhexyl)-xanthine are related methyl-xanthine derivatives which are well known in the art for treatment of a variety of disease states. PTX is widely used systemically for the treatment of peripheral vascular diseases. PTX and PPF have been administered systemically for the treatment of senile dementia while systemic administration of TBF is under investigation for treatment of senile dementia, peripheral vascular disease and myopathy.

PTX has been used systemically for the treatment of various cutaneous lesions associated with or due to impaired or deficient blood flow in the dermis layer of skin and its effectiveness in the treatment of peripheral vascular diseases is described by H. Ely, Dermatologic Clinics 6:585–608 (1988). There is no teaching that PTX, or any of its congeners, PPF or TBF, were effective in the treatment of psoriasis or atopic dermatitis, which are lesions of the epidermis layer of the skin rather than one of the peripheral blood vessels.

DETAILED DESCRIPTION OF THE INVENTION

Figure 1A:

In accordance with the present invention it has surprisingly been found that the topical administration of a pharmaceutical composition comprising a compound selected from the group of pentoxifylline, propentofylline and torbafylline dramatically improves the psoriatic lesions of patients. Most surprisingly the improvement is greater than that achieved with other xanthine derivatives such as dyphylline which are taught in the prior art as useful for the topical treatment of psoriatic lesions.

Accordingly, the present invention provides a pharmaceutical composition for the topical treatment of psoriasis or atopic dermatitis comprising an effective amount of an active compound selected from the group of pentoxifylline, propentofylline and torbafylline, and a pharmaceutically acceptable carrier.

Preferably the concentration of the active compound is about 0.5%–5% (w/w). When the active compound is pentoxifylline its concentration is preferably 2% (w/w).

If desired, the compositions according to the invention may additionally contain therapeutically effective amounts of one or more compound which are known to be of use in the topical treatment of psoriasis and atopic dermatitis. These compounds are well known to those skilled in the art and include cyclosporine, methotrexate, tamoxifen, forskolin and analogs, tar derivatives, steroids, vitamin A and its derivatives, vitamin D and its derivatives including 1-alpha-hydroxy-cholecalciferol, 1,25-dihydroxy-cholecalciferol, 24,25-dihydroxy-cholecalciferol, 1,24-dihydroxy-cholecalciferol and calcipotriol (MC 903), and beta agonists such as terbutaline.

In addition or instead, the compositions according to the invention may contain one or more of the compounds adenosine and related purines, lipoxygenase inhibitors, substance P antagonists, delta tocopherol, 2-heptanone, and fatty acids and their esters such as heptanoic acid, ethyl heptanoate, 3,3-dimethylbutyric acid, and lipoic acid.

The pharmaceutically acceptable carrier of the compositions according to the invention may contain any of the components which are used in topical compositions and are well known to those skilled in the art.

If desired, the pharmaceutically acceptable carrier of the compositions according to the invention may also contain penetration enhancers such as urea, lactic acid, ammonium lactate, salicylic acid or a $C_3$–$C_{12}$-straight chain alkanoic acid.

The compositions may be in the form of lotions, creams, ointments and gels, and also in the form of sprayable aerosols. Preferred formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, typically polyoxy-40-stearate.

The invention also provides a method for the treatment of a subject suffering from psoriasis or atopic dermatitis comprising topically applying to the subject a therapeutically effective amount of an active compound selected from the group consisting of pentoxifylline, propentofylline and torbafylline if desired together with a pharmaceutically acceptable carrier.

The preferred active compound for the performance of the method according to the invention is pentoxifylline.

If desired the said active compound may be applied together with a therapeutically effective amount of one or more additional compounds which are known to be of use in the topical treatment of psoriasis and atopic dermatitis. These compounds are well known to those skilled in the art and include cyclosporine, methotrexate, tamoxifen, forskolin and analogs thereof, tar derivatives, steroids, vitamin A and its derivatives, or vitamin D and its derivatives including 1-alpha-hydroxy-cholecalciferol, 1,25-dihydroxy-cholecalciferol24,25-dihydroxy-cholecalciferol, 1,24-dihydroxy-cholecalciferol and calcipotriol (MC 903), and beta agonists such as terbutaline.

Also if desired the said active substance may be applied together with an effective amount of at least one member of the group of adenosine and related purines, lipooxygenase inhibitors, substance P antagonists, delta tocopherol, 2-heptanone, and fatty acids and their esters such as heptanoic acid, ethyl heptanoate, 3,3-dimethylbutyric acid, and lipoic acid.

Still further the invention provides for use of a compound selected from the group consisting of pentoxifylline, propentofylline and torbafylline for the preparation of pharmaceutical compositions for the topical treatment of human patients suffering from psoriasis of atopic dermatitis.

BRIEF DESCRIPTION OF THE PICTURES

Figure 1B:
Figure 1C:
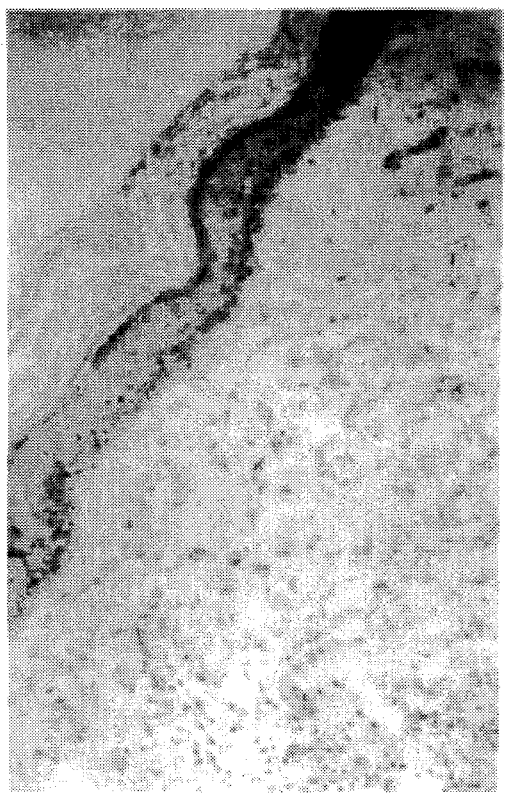
Figure 2A:
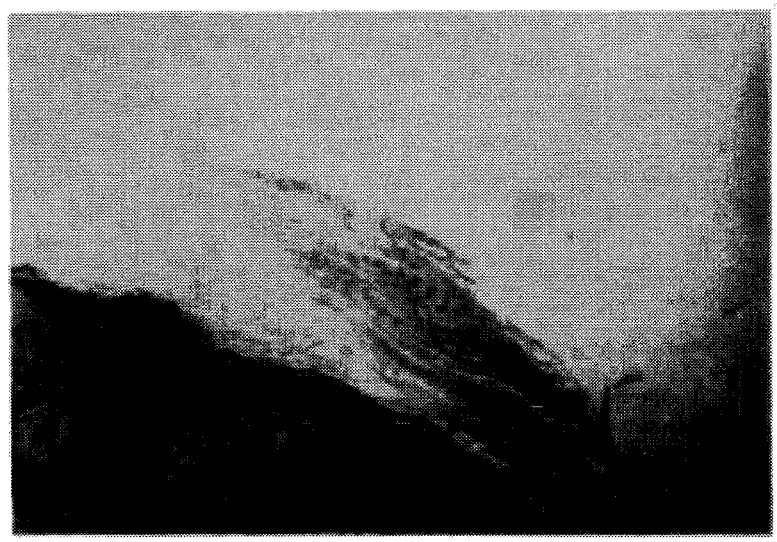
Figure 2B:

In the following Example 1 the advantages achieved in accordance with the invention are described, i.a. with reference to the annexed pictures in which:

FIG. 1 shows photomicrographs of transverse sections of human psoriatic skin transplants before and after treatment; and FIG. 2 shows two further similar photomicrographs.

Some embodiments of the present invention will now be described and exemplified in the following Examples, it being understood that the invention is not limited thereto.

EXAMPLE 1

Formulations

A. Pentoxifylline was formulated into a cream for topical application as follows:

|  | % w/w |
| --- | --- |
| Stearic Acid | 15.0 |
| Cetyl Alcohol | 1.0 |
| White Petrolatum | 3.0 |
| Polyoxy 40 Stearate | 4.0 |
| Methyl Paraben | 0.025 |
| Propyl Paraben | 0.015 |
| Pentoxifylline (PTX) | 2.0 |
| Propylene Glycol | 9.5 |
| Sorbitol | 7.5 |
| Purified Water | To make up 100% |

This formulation was used in Examples 2 and 5.

B. Additional cream formulations of pentoxifylline suitable for topical application was prepared as follows:

|  | % w/w |
| --- | --- |
| Pentoxifylline (PTX) | 2.0 |
| Urea | 5.0 |
| Lactic Acid | 2.0 |
| Germaben II | 1.0 |
| Sorbitol 70 solution | 4.0 |
| Glycerin | 4.0 |
| White Petrolatum | 3.0 |
| Glyceryl monostearate | 3.0 |
| Cetyl alcohol | 3.5 |
| Heavy mineral oil | 10.0 |
| Eutanol G-Octyldodecanol | 5.0 |
| Acetylated lanolin (Modulan ™) | 3.0 |
| Myrg 52 ™ | 3.0 |
| Span 60 ™ | 1.5 |
| Ammonia solution to adjust pH to | 4.5 |
| Water | To make up 100% |

C. Pentoxifylline was formulated into an ointment for topical application as follows:

|  | % w/w |
| --- | --- |
| Miglyol ™ 840-B Gel | 10.0 |
| Eutanol G-Octyldodecanol | 17.0 |
| Cril 6-Glyceryl isostearate | 3.0 |
| Hard paraffin wax | 3.0 |
| Zinc stearate | 1.0 |
| Amphisol K | 0.5 |
| Germaben II | 1.0 |
| Magnesium sulfate | 0.2 |
| Urea | 10.0 |
| Pentoxifylline (PTX) | 2.0 |
| Purified water | To make up to 100% |

D. Pentoxifylline was formulated into a gel suitable for topical application as follows:

|  | % w/w |
| --- | --- |
| Pentoxifylline (PTX) | 2.0 |
| Carbopol 940 ™ | 1.5 |
| Triethanolamine | 1.5 |
| Water | 95.0 |

EXAMPLE 2

Nude Mice with Transplanted Human Skin

Human psoriatic skin from psoriatic patients was transplanted to nude mice essentially according to the method of G. Kreuger et al., Prog. in Dermatol. 12:17–22 (1978) as modified by A. Gilhar et al., Exp. Cell Biol. 54:263–274 (1986). The donors had stable plaque type psoriasis for at least one year preceding biopsy and had not received systemic anti-psoriatic therapy for the 4 weeks preceding biopsy. They had also not received topical therapy or U.V. therapy for the two weeks preceding biopsy. The severity of the psoriatic lesion was evaluated and the PASI index was calculated as described by Fredrikson and Petterson (Dermatologica 157:238–244 (1978)). In this method the area (A) of the psoriasis in four main body parts (head (H), trunk (T), upper extremities (U) and lower extremities (L)) is assigned a value from 0–6 depending on the extent of psoriasis where O reflects no involvement and 6 reflects 90–100% involvement. The severity of the lesion is assessed based on three parameters: Erythema (E), Desquamation (scaling) (D) and Infiltration (I). The severity of each of these parameters is measured on a scale of 0–4 where 0 is no involvement and 4 is very sever. The total severity score is calculated according to the following formula:

$$\text{Severity score} = 0.1(E_H + I_H + D_H)A_H + 0.2(E_U + I_U + D_U)A_U + 0.3(E_T + I_T + D_T)A_T + 0.4(E_L + I_L + D_L)A_L$$

Split thickness biopsies of nonpustular psoriatic human tissue, 4×5 cm and 0.4 mm thick were obtained from the edge of established plaques from various donor patients. Each specimen was divided into sections as follows: 4–5 sections, 2×2 mm each for thymidine incorporation and subsequent autoradiography in order to assess the rate of proliferation in the epidermis; 1–2 sections 0.5×1 cm each for histological examination prior to grafting in order to evaluate the severity of the disease, as quantitated by the measure of epidermal thickness; and 3 sections 1.5×1 cm each for grafting on the dorsal side of each of three different nude mice. The grafts were allowed to heal for one week prior to topical application of the test preparations.

Outbred Balb/C nude mice, 2 to 3 months of age were used in this study. The mice were obtained from the pathogen free animal breeding facility at the University of Tel Aviv (Israel) and were raised in the pathogen-free animal facility at the Faculty of Medicine, Technion-Israel Institute of Technology, Haifa, Israel.

Following the one week healing period the graft area was treated daily with the test drug in a cream composition according to Example 1 or vehicle alone by applying 200 μl of the preparation, once at 08:00 and once at 21:00 for the duration of 7 days.

On the day following the end of treatment the severity of the psoriatic lesion was assessed and then the animals were sacrificed and the entire graft was excised and divided into two equal sections. One section was used to assess changes in the rate of proliferation by autoradiography (tritiated thymidine incorporation) while the other section was sectioned for microscopic histological assessment, including acanthosis and parakeratosis.

Table 1 shows the effect of the topical preparations tested on human psoriatic skin transplanted in nude mice according to the procedure outlined above. The results of the experiment shown in Table 1 demonstrate that pentoxifylline is almost as effective as steroids in treating psoriasis and far more effective than dyphylline, a related xanthine which was shown to be virtually inactive.

TABLE 1

Epidermal Thickness (Acanthosis) of Psoriatic Skin Transplants (in μm)*
% Improvement (Decrease in Thickness) Before and After Treatment With Various Preparations.

| Donor Patient No. | PASI** Score Before Treatment | | After 7 Days Treatment | | | | | | |
| --- | --- | --- | --- | --- | --- | --- | --- | --- | --- |
| | | | 2% PTX | | 8% Dyphylline | | 0.05% Clobetasol propionate*** | | Placebo |
| | | μm | μm | % Improv. | μm | % Improv. | μm | % Improv. | μm | % Improv. |
| 1 | 3.2 | 44 | | | 65 | 0 | 24 | 45 | | |
| 2 | 3.2 | 68 | | | | | | | 62 | 9 |
| 3 | 7.6 | 46 | 28 | 40 | | | 27 | 41 | | |
| 4 | 17.6 | 54 | 42 | 22 | | | 24 | 55 | | |

TABLE 1-continued

Epidermal Thickness (Acanthosis) of Psoriatic Skin
Transplants (in μm)*
% Improvement (Decrease in Thickness) Before and After
Treatment With Various Preparations.

| Donor Patient No. | PASI** Score Before Treatment | μm | 2% PTX μm | 2% PTX % Improv. | 8% Dyphylline μm | 8% Dyphylline % Improv. | 0.05% Clobetasol propionate*** μm | 0.05% Clobetasol propionate*** % Improv. | Placebo μm | Placebo % Improv. |
|---|---|---|---|---|---|---|---|---|---|---|
| 5 | 31.3 | 35 | | | 45 | 0 | 47 | 0 | | |
| 6 | 3.8 | 55 | 39 | 30 | | | | | 77 | 0 |
| Average Improvement | | | | 31% | | 0% | | 35% | | 5% |

*μ= micrometer
**PASI = Psoriasis Area Severity Index (see Example 3)
***Dermovate ™-Glaxo In another series of experiments, human psoriatic skin of various severities was transplanted on each of 28 nude mice. The graft area was treated with various preparations as described above.

Table 2 shows the results of the application of topical skin formulations to transplanted human psoriatic skin in each of the 28 nude mice. The results are expressed as a success ratio where success is defined as a decrease of at least 15% in epidermal thickness (acanthosis) as a result of the 7 day topical treatment. The treatments were applied as creams and were administered as described above.

The experiment shown in Table 2 demonstrates that pentoxifylline is almost as effective as topical steroids in treating psoriasis and far more effective than dyphylline which was inactive.

In summary the experiments performed with the animal model for psoriasis described above present a clear indication that PTX is effective in the treatment of psoriasis.

TABLE 2

| TREATMENT | SUCCESS RATIO |
|---|---|
| 2% Pentoxifylline* | 6/10 |
| 8% Dyphylline | 0/2 |
| 0.05% topical steroid** | 7/10 |
| Placebo | 0/6 |

*Cream composition prepared according to the formulation given in Example 1A.
**The topical steroid was either 0.05% clobetasol propionate ointment (Dermovate ™-Glaxo) or 0.05% betamethasone dipropionate cream (Diprosone ™ Schering U.S.A.).

FIG. 1 shows photomicrographs of representative examples of transverse human psoriatic skin transplant sections. The transplants were made as described above and were all taken from the same patient.

Panel A shows a transplant before treatment and panels B and C show transplants after daily treatments for seven days with the 2% PTX cream of Example 1 and an 0.05% clobetasol propionate ointment, respectively.

FIG. 2 shows similar photomicrographs before and after daily treatment for seven days with 8% dyphylline.

EXAMPLE 3

Inhibition of Human Psoriatic Fibroblast Proliferation

As excess proliferation of fibroblasts is one of the symptoms of psoriasis, the inhibition of fibroblasts proliferation was used as a test to determine the utility of the drugs of the present invention in the treatment of psoriasis. PTX and PPF, alone as well as PTX in combination with other drugs were tested.

Human psoriatic fibroblasts were obtained from skin biopsies of 5 individuals with plaque psoriasis. Cells in the 3-7th passages were used for the experiments. Human psoriatic fibroblasts ($4\times10^3$ –$6\times10^3$ cells) were added in 24-well plates and cultured in Dulbecco's Modified Eagle's Medium (DMEM) supplemented with 10% fetal calf serum, 2 mM L-glutamine, 100 u/ml penicillin, 100 μg/ml streptomycin (DMEM+) at 5% $CO_2$ and 95% humidity at 37° C.

After 3 days, medium was replaced with fresh DMEM+ (control) or with medium containing various concentrations of compounds alone or in combination with pentoxifylline and incubation was continued for additional 3 days. Stock solutions ($10^{-1}$–$10^{-2}$ M) of the compounds tested were made in ethanol. For these compounds special control (DMEM+ with 1% ethanol) was made. The compounds tested together with pentoxifylline were 3-heptanone, 3,3-dimethylbutyric acid, lipoic acid, 1,25-dihydroxyvitamin $D_3$ betamethasone dipropionate and hydrocortisone-17-butyrate.

On the last day of experiments, the medium was aspirated and the cells were obtained by trypsinization. The number of cells in each well was counted by the use of an hemocytometer.

The percentage of inhibition of fibroblast proliferation was calculated according to the formula:

$$100 - \frac{\text{amount of fibroblasts in the well in the presence of the drug}}{\text{amount of fibroblasts in the well in the absence of the drug}} \times 100$$

and the results are shown in Tables 3 and 4.

TABLE 3

| Compound | Concentration of additional drug (M) | % Inhibition of Proliferation PTX $10^{-4}$ (M) | % Inhibition of Proliferation PTX $10^{-3}$ (M) |
|---|---|---|---|
| Pentoxifylline (PTX) | | 3.7 | 16.9 |
| 2-Heptanone | $10^{-5}$ | N.D. | 21.3 |
| | $10^{-4}$ | 21.0 | 26.4 |
| | $10^{-3}$ | 18.6 | 45 |
| 3,3dimethyl butyricacid | $10^{-4}$ | 19.3 | 17.2 |
| | $10^{-3}$ | 36.3 | 21 |
| Lipoicacid | $10^{-4}$ | 14.5 | 50.2 |
| 1,25(OH)$_2$D$_3$ | $10^{-7}$ | 49.5 | N.D. |
| Betamethasone dipropionate | $10^{-7}$ | 43.1 | N.D. |
| | $10^{-4}$ | 55.8 | 77.5 |

TABLE 3-continued

| Compound | Concentration of additional drug (M) | % Inhibition of Proliferation PTX $10^{-4}$ (M) | PTX $10^{-3}$ (M) |
| --- | --- | --- | --- |
| hydrocortisone | $10^{-5}$ | N.D. | 41.9 |
| 17-butyrate | $10^{-5}$ | N.D. | 51.2 |

N.D. = Not Determined
$1,25(OH_2)D_3$ is 1,25-dihydroxyvitamin $D_3$

TABLE 4

| Compound | Concentration (M) | % Inhibition of Proliferation |
| --- | --- | --- |
| Pentoxifylline (PTX) | $10^{-4}$ | 5.9 |
|  | $10^{-3}$ | 16.9 ± 4.8 |
| Propentofylline (PPF) | $10^{-4}$ | 20.3 ± 6.6 |
|  | $10^{-3}$ | 39.0 ± 7 |

These results show that the drugs of the present invention do inhibit the proliferation of fibroblasts which indicate their potential utility in treating psoriasis. The results are satisfactory both when these drugs are applied as the only active compound and when they are applied in combination with other drugs.

EXAMPLE 4

Inhibition of the Mitogenic Stimulation of Human Lymphocytes

Study in the literature have shown that atopic dermatitis is transferable by bone marrow cells indicating that primary site of disease is in the immune and inflammatory cells which infiltrate the skin. Thus the lymphocytes are thought to be one of the targets for treatment of the disease. Also, various cells (including lymphocytes) and organs derived from atopic subjects showed a common impaired response to cAMP agonists. Thus the study of atopic lymphocytes behavior in response to various agents is predictive of the atopic individuals response to these agents.

Studies have shown that cAMP agonists have an inhibitory effect on the mitogenic stimulation of peripheral blood mononuclear cells (PBMC) from atopic subjects (Ravid et al., J. Allergy Clin. Immunol. 86:881–885 (1990)). In these studies it was found that those compounds which have an inhibitory effect on PBMC from atopic subjects have a similar inhibitory effect on PBMC from healthy subjects. The primary difference noted was one of degree; the inhibitory effect on cells from atopic subjects was reduced when compared to healthy individuals. It was also shown that steroids such as dexamethasone, which are used in the treatment of atopic dermatitis, inhibited the mitogenic stimulation of PBMC. Thus the inhibitory effect of certain compounds on the mitogenic stimulation of PBMC isolated from healthy and atopic individuals is predictive of the effect of these compounds in the treatment of atopic diseases, including atopic dermatitis.

All materials and tissue culture media used were obtained from commercial sources.

Buffy coats from the Beilinson Medical Center Blood Bank or 20 mL samples of heparinized venous blood from healthy or atopic donors were used as a source for human peripheral blood mononuclear (PBM) cells. PBM cells were separated by Ficoll-Hypaque density gradient centrifugation. Partial depletion of adherent cells was achieved by incubating PBM cells for 90 min in plastic petri dishes at 37° C. at a concentration of $5 \times 10^4$ cells/mL in RPMI-1640 medium containing 2% heat-inactivated newborn calf serum. The nonadhering cells were stirred gently and carefully collected. The monocyte content of PBM cells was thus reduced to 3–7%.

PBM cells were suspended ($1 \times 10^4$/mL) in RPMI-1640 medium containing 5% heat-inactivated pooled human AB serum supplemented with penicillin (100 U/mL) and streptomycin (100 µg/mL). Cells were incubated at 37° C. in a humidified 5% $CO_2$- 95% air atmosphere in 0.2 mL aliquots in 96-well flat bottomed Cooke microtiter plates. PHA (1 µg/mL), indomethacin (5 µg/mL) and various xanthine derivatives were added at initiation of culture. Indomethacin was dissolved in ethanol. The concentration of ethanol in the cell cultures did not exceed 0.006%, a concentration that, in our hands, has no effect on any of the cellular functions studied in this work. [methyl-$^3$H]Thymidine (1 µCi/well) was added at 68 h, and the cells were harvested 4 h later using an automated cell harvester (Dynatech, Alexandria, Va.). Unless otherwise stated, all cultures were performed in triplicate.

The inhibition of the mitogenic stimulation of PBMC by pentoxyfilline was found to be similar regardless of whether the source of the cells was patients with atopic dermatitis or healthy volunteers.

The net inhibitory effect on the mitogenic stimulation of human lymphocytes from healthy volunteers was compared for pentoxyfilline, propentofylline and two other xanthine derivatives, theophylline and diphylline (Table 5). Surprisingly, pentoxyfilline and propentofylline inhibited the mitogenic stimulation to a far greater effect than the other xanthine derivatives.

TABLE 5

| Concentration (M) | Xanthine Deriative Used | | | |
| --- | --- | --- | --- | --- |
|  | PPF | PTX | THEOP | DIPHY |
| $3 \times 10^{-4}$ | 88 | 46 | 37 | 12 |
| $1 \times 10^{-3}$ | 89 | 70 | 59 | 24 |

PPF-Propentofylline
PTX-Pentoxifylline
THEOP-Theophylline
DIPHY-Diphylline

EXAMPLE 5

Clinical Trial

A clinical trial was performed comparing a cream composition of 2% pentoxifylline (formulation A of Example 1) to placebo. The trial was randomized, double blind, placebo controlled, right-left comparison within patient design.

Two similar plaque areas of psoriasis (i.e. both legs or forearms), were selected for treatment in each patient. In each patient one area on one side of the body was treated with 2% pentoxifylline formulated as in Example 1 and the other area on the other side of the body was treated with placebo cream formulated identically but without the pentoxifylline. The cream (formulation A in Example 1) was applied by the patient twice daily.

Patients were selected so that the lesions did not cover more than 30% of the total skin area. Patients stopped all forms of topical psoriatic treatment two weeks before entry into the study.

Systemic psoriatic treatments and phototherapy were stopped one month before entry into the study.

The dermatological assessment was performed as follows. The dermatologist measured the area of the lesion in cm$^2$. The severity of each lesion was evaluated by grading erythema, scaling and thickness on a 0-4 scale where 0=none, 1=slight, 2=moderate, 3=severe and 4=exceptionally severe.

Based on these measurements the Psoriasis Area Severity Index (PASI) was calculated for each of the 2 lesions on each patient as follows:

PASI=Area x (Erythema+Thickness+Scaling)

Patient 1: After 1.5 weeks of treatment the patient showed a 58% decrease in PASI on the pentoxifylline treated side and 0% decrease in PASI on the placebo treated side.

Patient 2: After 2 weeks of treatment the patient showed a 53% decrease in PASI on the pentoxifylline treated side and 34% decrease in PASI on the placebo treated side.

Patient 3: After 2 weeks of treatment the patient showed a 73% decrease in PASI on the pentoxifylline treated side and 45% decrease in PASI on the placebo treated side. After 6 weeks of treatment the decrease in PASI on the pentoxifylline treated side was 90% and on the placebo treated side 56%.

Patient 4: After 6 weeks of treatment the patient showed a 91% decrease in PASI on the pentoxifylline treated side and 73% decrease in PASI on the placebo treated side. After 8 weeks of treatment the decrease in PASI on the pentoxifylline treated side was 88% and on the placebo treated side 57%.

Patient 5: After 2 weeks of treatment the patient showed a 73% decrease in PASI on the pentoxifylline treated side and 25% decrease in PASI on the placebo treated side.

In all patients the improvement in erythema was most pronounced. There was also good improvement in the thickness scores.

EXAMPLE 6

Clinical Trial

In a different series of tests 5% dyphylline cream was applied in the same vehicle that had been used to apply PTX cream. Thus the formulation used in this series of tests was the same as in Example 1 with the exception that 5% dyphylline was used in place of 2% pentoxifylline. The design of the trial was similar in all respects to the clinical trial of PTX described in Example 5 except that the number of patients was 33. The results shown in Table 6 demonstrate that treatment with dyphylline was nearly ineffective with respect to placebo.

Treatment with 5% dyphylline vs. Placebo % Decrease in PASI as a Function of Time (n = 33 patients)

|  | 1 week | 2 weeks | 4 weeks | 6 weeks |
| --- | --- | --- | --- | --- |
| 5% Dyphylline | 12.6 | 25.9 | 28.0 | 26.5 |
| Placebo | 12.4 | 30.0 | 21.5 | 15.6 |

In summary the clinical trials demonstrate that topical pentoxifylline, a xanthine derivative, is a very effective therapeutic for the treatment of psoriatic lesions. However, dyphylline, a different xanthine derivative is virtually inactive in the treatment of psoriasis. These clinical trials also demonstrate the close correlation between the results obtained in the animal model and the results obtained in the clinical trial.

EXAMPLE 7

Clinical Trials

A randomized double blind, vehicle controlled, bilateral comparison study was performed, to determine the effect of pentoxifylline (PTX) in the treatment of atopic dermatitis. The study medication contained 2% pentoxifylline in an oil-in-water cream vehicle, and the control treatment consisted of the same vehicle without the pentoxifylline. The exact formulations appear in Table 7.

Seven patients (aged 3-10 years) were enrolled in the trial and evaluated for pruritus, erythema, dryness/scaling and exudate. Pentoxifylline cream, or the placebo (the identical cream, but without the pentoxifylline) were dispensed in identical tubes that were marked for application to right and left sides. Patients were instructed to apply medication twice a day (morning and evening) for four weeks.

The patients were evaluated at the end of the four week period and the results demonstrated that the pentoxifylline treatment significantly improved each of the four symptoms evaluated.

TABLE 7

| INGREDIENT | TEST CREAM % W/W | PLACEBO % W/W |
| --- | --- | --- |
| Pentoxifylline | 2.0 |  |
| Urea | 5.0 | 5.0 |
| Lactic acid | 2.0 | 2.0 |
| Ammonia | 1.0 | 1.0 |
| Germaben ii | 1.0 | 1.0 |
| Sorbitol 70% | 4.0 | 4.0 |
| Glycerol | 4.0 | 4.0 |
| White petrolatum | 3.0 | 3.0 |
| Glyeryl monostearate | 3.5 | 3.5 |
| Cetyl alcohol | 3.5 | 3.5 |
| Mineral oil | 10.0 | 10.0 |
| Octyldecanol | 5.0 | 5.0 |
| Acetylated lanolin | 3.0 | 3.0 |
| Polyoxyl 40 stearate | 3.0 | 3.0 |
| Sorbitan monostearate | 1.5 | 1.5 |
| Purified water | 64.5 | 66.5 |

We claim:

1. A composition for the topical treatment of psoriasis or atopic dermatitis comprising an effective amount of an active compound selected from the group consisting of propentofylline and torbafylline, and a pharmaceutically acceptable topical carrier, said composition being in the form of lotion, cream, ointment, encapsulated gel or sprayable aerosol.

2. A method for the treatment of a subject suffering from psoriasis or atopic dermatitis, comprising topically applying to said subject a therapeutically effective amount of an active compound selected from the group consisting of pentoxifylline, propentofylline and torbafylline.

3. The method of claim 2, wherein said active compound is pentoxifylline.

4. The method of claim 3, wherein said active substance is applied together with a pharmaceutically acceptable topical carrier.

* * * * *